US005859069A

United States Patent [19]

Yanagida

[11] Patent Number: 5,859,069

[45] Date of Patent: Jan. 12, 1999

[54] GELATINOUS EXTERNAL SKIN TREATMENT COMPOSITION

[75] Inventor: Takeshi Yanagida, Yokohama, Japan

[73] Assignee: Shiseido Company, Ltd., Tokyo, Japan

[21] Appl. No.: 943,695

[22] Filed: Oct. 3, 1997

[30] Foreign Application Priority Data

Oct. 3, 1996 [JP] Japan .................................... 8-281791

[51] Int. Cl.[6] .......................... A61K 31/695; A61K 47/30

[52] U.S. Cl. .................................... 514/772.3; 424/78.03; 514/63

[58] Field of Search .................................... 514/63, 772.3

[56] References Cited

FOREIGN PATENT DOCUMENTS

| | | |
|---|---|---|
| 2-243612 | 9/1990 | Japan . |
| 4-17162 | 3/1992 | Japan . |
| 4-66446 | 10/1992 | Japan . |
| 9-183710 | 7/1997 | Japan . |

OTHER PUBLICATIONS

Chemical Abstracts 121:212653g (Kuroda et al), 1994.
Chemical Abstracts 123:321721q (Hineno et al), 1995.

*Primary Examiner*—Leonard Schenkman
*Attorney, Agent, or Firm*—Foley & Lardner

[57] ABSTRACT

A gelatinous external skin treatment composition comprising (1) spherical powder of organopolysiloxane elastomer having an average particle size of 1.0 to 15.0 $\mu$m, (2) silicone oil and (3) polyether modified silicone having the formula (I):

$$A-\underset{R}{\overset{R}{\underset{|}{\overset{|}{Si}}}}O-\left[\underset{R}{\overset{R}{\underset{|}{\overset{|}{Si}}}}O\right]_m-\left[\underset{B}{\overset{R}{\underset{|}{\overset{|}{Si}}}}O\right]_n-\underset{R}{\overset{R}{\underset{|}{\overset{|}{Si}}}}-A \quad (I)$$

wherein A represents a methyl group, phenyl group, or B explained below, B is a polyoxyalkylene group having the formula:

$$-C_3H_6O(C_2H_4O)_a(C_3H_6O)_bR',$$

wherein R' is a group selected from the group consisting of a hydrogen atom, acyl group, and $C_1$ to $C_4$ alkyl groups, a is an integer of 5 to 50, and b is an integer of 5 to 50, R is a methyl group or phenyl group, m is an integer of 50 to 1000, and n is an integer of 0 to 40, provided that at least one polyoxyalkylene group is present in the molecule, and optionally (4) a lower alcohol having 3 carbon atoms or less and/or water.

4 Claims, No Drawings

GELATINOUS EXTERNAL SKIN TREATMENT COMPOSITION

BACKGROUND OF THE INVENTION

1. Field of the Invention

The present invention relates to a gelatinous external skin treatment composition (e.g., make-up cosmetics) containing silicone oil formulated therein in a gelatinous (or gelatinized) form and having good useability.

2. Description of the Related Art

In the recent years, in the field of external skin treatment agents, wide use has been made of silicone oils as oil components giving a light spreadability at the time of use and with little stickiness. There have been few satisfactory methods for gelatinizing silicone oil base agent. One relatively simple method has been proposed to use the solidifying action of waxes, but the use of a wax results in a heavy spreadability and stickiness, and therefore, in many cases, the characteristic feeling of use according to silicone oil is lost.

In the case of cosmetic compositions including make-up cosmetics, one of the important factors is the persistence of cosmetic effects, or cosmetic persistency, in addition to the effects providing the skin conditionings and beautiful appearances. According to the known techniques for improving the cosmetic persistency, hydrophobically treated powders or silicone resins are formulated in cosmetic compositions. In the case of the hydrophobically treated powders, only a relatively short period of time after the application is effective, there are disadvantages that the effects are not large when the sweat or the sebum is largely generated in summer or during sports. In the case of the silicone resins, although the cosmetic persistency is exhibited unlike the use of the hydrophobically treated powders, there are disadvantageous in that the feelings of film are provided.

SUMMARY OF THE INVENTION

Accordingly, the objects of the present invention are to eliminate the above-mentioned disadvantageous of the prior art and to provide a gelatinous external skin treatment composition.

Other objects and advantages of the present invention will be apparent from the following description.

In accordance with the present invention, there is provided a gelatinous external skin treatment composition comprising (1) 1.0 to 20.0% by weight of spherical powder of organopolysiloxane elastomer having an average particle size of 1.0 to 15.0 μm, (2) 5.0 to 75.0% by weight of silicone oil and (3) 1.0 to 20.0% by weight of polyether modified silicone having the formula (I):

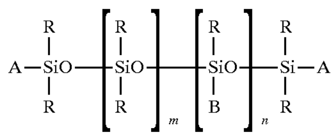

(I)

wherein A represents a methyl group, phenyl group, or B explained below, B is a polyoxyalkylene group having the formula:

$$—C_3H_6O(C_2H_4O)_a(C_3H_6O)_bR'$$

wherein R' is a group selected from the group consisting of a hydrogen atom, acyl group, and $C_1$ to $C_4$ alkyl groups, a is an integer of 5 to 50, and b is an integer of 5 to 50, R is a methyl group or phenyl group, m is an integer of 50 to 1000, and n is an integer of 0 to 40, provided that at least one polyoxyalkylene group is present in the molecule.

In accordance with the present invention, there is also provided a gelatinous external skin treatment composition comprising:

(1) 1.0 to 20.0% by weight of spherical powder of organopolysiloxane elastomer having an average particle size of 1.0 to 15.0 μm;

(2) 25.0 to 85.0% by weight of silicone oil;

(3) 1.0 to 30.0% by weight of a polyether modified silicone having the general formula (I):

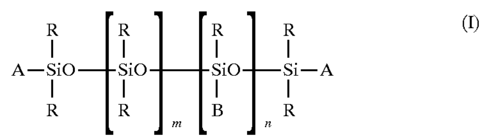

(I)

wherein A represents a methyl group, phenyl group, or B explained below, B is a polyoxyalkylene group having the formula:

$$—C_3H_6O(C_2H_4O)_a(C_3H_6O)_bR'$$

wherein R' is a group selected from the group consisting of a hydrogen atom, acyl group, and $C_1$ to $C_4$ alkyl groups, a is an integer of 5 to 50, and b is an integer of 5 to 50, R is a methyl group or phenyl group, m is an integer of 50 to 1000, and n is an integer of 0 to 40, provided that at least one polyoxyalkylene group is present in the molecule; and (4) 1.0 to 15.0% by weight of a component selected from the group consisting of lower alcohols having 3 carbon atoms or less and water.

DESCRIPTION OF THE PREFERRED EMBODIMENTS

The present inventors engaged in intensive research in view of the above situation and, as a result, found that, when (1) spherical powder of an organopolysiloxane elastomer having an average particle size of 1.0 to 15.0 μm, (2) a silicone oil, and (3) a specific polyether modified silicone are formulated, a make-up cosmetic composition having an excellent cosmetic persistency effect can be obtained, whereby the first embodiment of the present invention is accomplished.

The present inventors further engaged in intensive research in view of the above situation and, as a result, found that, when (1) spherical powder of an organopolysiloxane elastomer having an average particle size of 1.0 to 15.0 μm, (2) a silicone oil, (3) a specific polyether modified silicone, and (4) a lower alcohol having 3 carbon atoms or less and/or water are formulated, a gelatinous external skin treatment composition having a superior useability can be obtained, whereby the second embodiment of the present invention is accomplished. Note that the applicant of this application previously developed a gelatinous cosmetic composition comprised of a silicone oil, polyether modified silicone, water, and a hydrophobic powder (Japanese Patent Application No. 8-21872), but the present invention further improves on this technology.

The present invention will now be explained in detail below.

As the spherical powder of organopolysiloxane elastomer formulated in the gelatinous external skin treatment composition of the present invention, those described in Japanese Examined Patent Publication (Kokoku) No. 4-66446, Japanese Unexamined Patent Publication (Kokai) No. 2-243612, and Japanese Examined Patent Publication (Kokoku) No. 4-17162 are exemplified. It is easy to use those commercially available under the brand name, for example, Torayfil E-506C or Torayfil E-505C from Toray-Dow Corning Corporation.

Further, those having an average particle size of 1.0 to 15.0 μm, preferably 1.0 to 10.0 μm are effective in the present invention. Those having a size of less than 1.0 μm does not bring out the effect of the present invention. Further, those having a size of more than 15.0 μm gives a rough feeling and is not suitable as a material for an external skin treatment composition.

The amount of the organopolysiloxane elastomer spherical powder formulated in the gelatinous external skin treatment composition of the present invention has to be at least 1.0% by weight. If less than 1.0% by weight, the gelatination action is insufficient and therefore, is not preferred. To sufficiently bring out the effect of the present invention, at least 3.0% by weight is preferable. There is no particular upper limit on the amount blended from the viewpoint of the effect of the present invention, but when an especially large amount is formulated, in many cases “uneven finish” occurs during application, and therefore, is not preferable. If a limit has to be placed, it would be not more than 20.0% by weight.

In the case of a make-up cosmetic composition, the silicone oil used in the present invention include, for example, dimethyl polysiloxane and methyphenyl polysiloxane, as well as dimethyl cyclopolysiloxanes such as hexamethyl cyclotrisiloxane, octamethyl cyclotetrasiloxane, decamethyl cyclopentasiloxane, and dodecamethyl cyclohexasiloxane. Mixtures thereof may also be used.

Among these, a particularly preferable silicone oil is volatile dimethyl cyclopolysiloxane. Especially, in the case of a make-up cosmetic composition, when only non-volatile silicone oil is used, the cosmetic persistency is not satisfactory improved and sometimes, a rough feeling is given.

If the amount of the silicone oil formulated in the present invention is especially small, the mixing ability or suspendability with the spherical powder of organopolysiloxane elastomer and other powder ingredients are inferior and the productivity is poor. Further, there is no particular upper limit, in view of the effect of the present invention, but the formulation an especially large amount of the powder is not preferable from the viewpoint of the balance with other ingredients. Preferably, it is 25.0 to 85.0% by weight, particularly preferably 30.0 to 60.0% by weight, in the case of the external skin treatment composition. In the case of the make-up cosmetic composition, the powder is preferably formulated in an amount of 5.0–75.0% by weight.

The polyether modified silicone used in the present invention is an organopolysiloxane graft polymer of the general formula (I) having a polyoxyalkylene group.

The acyl group of R' specifically includes, for example, a formyl group, acetyl group, propionyl group, butyryl group, acryolyl group, benzoyl group, toluoyl group. The $C_1$ to $C_4$ alkyl group specifically includes, for example, a methyl group, ethyl group, i-propyl group, n-propyl group, t-butyl group, n-butyl group.

Note that, in the polyoxyalkylene group, of the formula (I), if a or b is less than 5, the polyether modified siloxane does not exhibit a sufficient thickening effect. Further, if a or b is more than 50, the resultant gelatinous external skin treatment composition has an undesirable sticky feel.

The content of the polyoxyalkylene group is not particularly limited, but the content of the polyoxyalkylene group is preferably more than 20% by weight, but not more than 70% by weight. This is because, when the content of the polyoxyalkylene group is 20% by weight or less, the thickening effect of the polyether modified silicone is remarkably decreased. On the other hand, when more than 70% by weight, the compatibility with silicone oil is decreased.

Further, m is an integer of 50 to 1000 and n is an integer of 0 to 40 (note: n is an integer of 1 to 40, in the case of a make-up cosmetic). Preferably, m is 200 to 600 and n is 5 to 20. This is because, when m is less than 50, the thickening effect is insufficient. Further, when m is more than 1000 and n is more than 40, the resultant gelatinous external skin treatment composition tends to have a sticky feeling.

The molecular weight of the polyether modified silicone used in the present invention is not particularly limited and the viscosity at 25° C. is not particularly limited either. However, in order to particularly stabilige the gelatinous external skin treatment composition, the polyether modified silicone used in the present invention preferably has a viscosity at the time of a 50.0% by weight solution of octamethyl tetrasiloxane in the range of 1000 to 100,000 cst. Further, the molecular weight is at least 50,000, preferably in the range of 50,000 to 80,000 from the viewpoint of stability and useability.

The amount of the polyether modified silicone used in the present invention should be at least 1.0% by weight preferably at least 2.0% by weight. If less than 1.0% by weight, the gelation becomes insufficient and the improvement in the cosmetic persistency tends to become poor in the case of a make-up cosmetic when the amount is less than 2.0% by weight. There is no particular upper limit on the amount from the viewpoint of the effect of the present invention, but is an especially large amount is blended, the “spreadability” at the time of application becomes heavy and stickiness is caused and the finishing becomes not natural in the case of a make-up cosmetic, and therefore, this is not preferable. If a limit has to be given, it would be not more than 30.0% by weight, preferably not more than 20.0% by weight.

The lower alcohol having 3 carbon atoms or less atoms used in the present invention includes, for example, ethyl alcohol, isopropyl alcohol, n-propyl alcohol. The amount of the lower alcohol and/or water optionally formulated is 1.0 to 15.0% by weight, preferably 5.0 to 12.0% by weight. If less than 1.0% by weight, the effect of the present invention is difficult to obtain, while if more than 15.0% by weight, the gel tends to be destroyed.

In the present invention, in addition to the above essential ingredients, it is of course possible to formulate a pigment, oil, surfactant, or humectant normally used in an external skin treatment composition as a substrate or a preservative, fragrance, chelating agent, antioxidant, ultraviolet absorber, etc. Furthermore, water, lower alcohol, gelling agent, thickening agent conventionally used in the make-up cosmetic may also be formulated.

Among the pigments, as examples of a powder other than the spherical powder of organopolysiloxane elastomer, inorganic pigments such as talc, kaolin, calcium carbonate, zinc white, titanium dioxide, red iron oxide, yellow iron oxide, black iron oxide, ultramarine, titanium coated mica, bismuth oxychloride, bengara, carcinated pigments, ultramarine pink, chromium hydroxide, titanated mica, chromium oxide, cobalt aluminum oxide, Prussian blue, carbon black, anhydrous silicic acid, magnesium silicate, bentonite, mica, zirconium oxide, magnesium oxide, etc. may be mentioned.

The organic pigments include, for example, powders of polyethylene, polypropylene, nylon, methyl methacrylate polymer, polystyrene, polystyrene-polyacrylic acid copolymer, vinyl chloride polymer, tetrafluoroethylene polymer, etc. and cellulose powder, chitan powder, chitosan powder, fish scale flake, tar colors.

These pigments may be subjected to surface treatment such as hydrophobization treatment. For example, high viscosity silicone oil treatment, silicone resin treatment based on an alkylhydrogen polysiloxane reaction, alkenation treatment, cationic activation, anionic activation, nonionic activation, waxing, dextrin fatty acid treatment, fluorine treatment, etc. may be mentioned.

As an oil component other than the silicone oil able to be formulated in the gelatinous external skin treatment composition according to the present invention, avocado oil, tsubaki oil, turtle oil, macadamia nut oil, corn oil, mink oil, olive oil, rapeseed oil, egg yoke oil, sesame oil, wheat germ oil, sasanqua oil, castor oil, linseed oil, safflower oil, cottonseed oil, perilla oil, soybean oil, peanut oil, teaseed oil, kaya oil, rice bran oil, shinagiri oil, hikiri oil, jojoba oil, germ oil, triglycerin, glyceryl trioctanate, glyceryl triisopalmitate, and other liquid oil components, cacao butter, coconut oil, beef tallow, hydrogenated coconut oil, palm oil, horse tallow, sheep tallow, hydrogenated beef tallow, palm kernal oil, lard, ox bone fat, Japan wax nut oil, hydrogenated oil, ox foot oil, Japan wax, hydrogenated castor oil, and other solid oil ingredients, beeswax, candelilla wax, cotton wax, carnauba wax, beverly wax, ibota wax, spermaceti, montan wax, nuka wax, lanolin, kapok wax, lanolin acetate, liquid lanolin, sugarcane wax, lanolin fatty acid isopropyl ester, hexyl laurate, hydrogenated lanolin, jojoba wax, hard lanolin shellac wax, POE lanolin alcohol ether, POE lanolin alcohol acetate, POE cholesterol ether, lanolin fatty acid polyethylene glycol, POE hydrogenated lanolin alcohol ether, etc. or liquid paraffin, ozokerite, squalane, pristane, paraffin, cerisin, squalene, vaseline, microcrystalline wax, and other hydrocarbon oils, etc. may be formulated. However, the ratio of the silicone oil, the volatile silicone oil in the case of the make-up cosmetic, in the oil ingredient as a whole must be at least 33% by weight. Further, from the viewpoint of the useability, it is desirable substantially not to blend in a wax ingredient.

EXAMPLES

The present invention will now be further illustrated by, but is by no means limited to, the following Examples.

Example I-1 and Comparative Examples I-1 to I-4

Creamy foundations were prepared by the formulations in Table I-1 by the following method and the cosmetic persistency was evaluated.

TABLE I-1

| | Example | Comparative Examples | | | |
|---|---|---|---|---|---|
| | 1 | 1 | 2 | 3 | 4 |
| (1) Torayfil E-506C (made by Toray Dow Corning) | 10.0 | — | — | 10.0 | 10.0 |
| (2) Polyethylene powder | — | 10.0 | 10.0 | — | — |
| (3) Octamethyl cyclotetrasiloxane | 50.0 | — | 50.0 | — | 50.0 |
| (4) Dimethyl polysiloxane (10 cs) | — | 50.0 | — | 50.0 | — |
| (5) Polyether modified silicone*1 | 10.0 | 10.0 | 10.0 | 10.0 | — |
| (6) Dimethyl polysiloxane (5000 cs) | — | — | — | — | 10.0 |
| (7) Silicone treated powder preparation | 20.0 | 20.0 | 20.0 | 20.0 | 20.0 |
| (8) Silicone treated ultrafine $TiO_2$ powder | 2.0 | 2.0 | 2.0 | 2.0 | 2.0 |
| (9) Methylparabene | 0.1 | 0.1 | 0.1 | 0.1 | 0.1 |
| (10) Purified water | 7.9 | 7.9 | 7.9 | 7.9 | 7.9 |

$$^{*1}CH_3-\underset{CH_3}{\overset{CH_3}{|}}{SiO}-\left[\underset{CH_3}{\overset{CH_3}{|}}{SiO}\right]_{400}-\left[\underset{(CH_2)_3O(C_2H_4O)_{24}(C_3H_6O)_{24}H}{\overset{CH_3}{|}}{SiO}\right]_{10}-\underset{CH_3}{\overset{CH_3}{|}}{Si}-CH_3$$

As a 50% decamethyl cyclopentasiloxane solution (but 50% light liquid paraffin solution in Comparative Example 3)

Method of Preparation

The ingredients (1), (7) and (8) were dispersed in the ingredient (3) or (4). Thereafter, (4) or (3) and (5)–(6) were added and dissolved with stirring. Then, an aqueous phase obtained by dissolving (9) in (10) was added thereto with stirring. After deaerating, the creamy foundation was obtained.

Evaluation of Cosmetic Persistency

The samples of Example I-1 and Comparative Examples I-1 to I-4 were evaluated by a panel consisting of 10 women member at the ages of 22–25. After applying to the faces, the panel members run in the distance of 2 km. Thereafter, the disorder of the cosmetic was self-evaluated. The results are shown in Table I-2.

TABLE I-2

| | Example I-1 | Comparative Example | | | |
|---|---|---|---|---|---|
| | | I-1 | I-2 | I-3 | I-4 |
| Number of members self-evaluated as cosmetic being disordered | 1 | 8 | 9 | 7 | 4 |

As is clear from the results shown in Table I-2, only one member evaluated to be disordered for the sample of Example I-1, 4 to 9 members evaluated to be disordered for the samples of Comparative Examples I-1 to I-4. This clearly means that the cosmetic of the present invention has an improved cosmetic persistency when compared with the conventionals.

Example I-2

Powdery Foundation

| | |
|---|---|
| (1) Talc | Balance |
| (2) Sericite | 15.0 wt % |
| (3) Mica | 20.0 |
| (4) Titanium dioxide | 10.0 |
| (5) Colored pigment | 5.0 |
| (6) Torayfil E-506C | 2.0 |
| (7) Dimethyl polysiloxane (6 cs) | 5.0 |
| (8) Glyceryl trioctanoate | 5.0 |
| (9) Polyether modified silicone*[1] | 10.0 |
| (10) Ethyl parabene | q.s. |
| | 100.0 |

*[1]See Table I-1

Method of Preparation

The ingredients (1)–(6) were mixed and ground, and then, were added to a liquid portion obtained by mixing (7)–(10), followed by kneading. Again, the mixture was subjected to the grinding treatment and, then, was sieved, followed by molding in a container.

Example I-3

Dual-Purpose Foundation

| | |
|---|---|
| (1) Silicone treated talc | Balance |
| (2) Silicone treated sericite | 15.0 wt % |
| (3) Silicone treated mica | 13.0 |
| (4) Silicone treated titanium dioxide | 16.0 |
| (5) Silicone treated colored pigment | 6.0 |
| (6) Torayfil E-506C | 20.0 |
| (7) Decamethyl cyclopentasiloxane | 5.0 |
| (8) Polyether modified silicone*[1] | 4.0 |
| (9) Methylphenyl polysiloxane | 4.0 |
| (10) Sorbitan sesquioleate | 1.0 |
| (11) Preservative | q.s. |
| (12) Fragrance | q.s. |
| | 100.0 |

*[1]See Table I-1

Method of Preparation

After mixing and grinding, the ingredients (1)–(6) were added to a liquid portion obtained by mixing (7)–(12), followed by kneading the mixture. The mixture was again ground and, after subjecting to a sieving treatment, molded in a container.

Example I-4

Liquid Foundation

| | |
|---|---|
| (1) Silicone treated talc | 5.0 wt % |
| (2) Silicone treated sericite | 3.0 |
| (3) Silicone treated mica | 3.0 |
| (4) Silicone treated titanium dioxide | 6.0 |
| (5) Silicone treated colored pigment | 3.0 |
| (6) Torayfil E-506C | 2.0 |
| (7) Decamethyl cyclopentasiloxane | 72.0 |
| (8) Polyether modified silicone*[1] | 4.0 |
| (9) Diglyceryl diisostearate | 1.0 |
| (10) Dimethyl polysiloxane (6 cs) | 1.0 |
| (11) Preservative | q.s. |

*[1]See Table I-1

Method of Preparation

The ingredients (1)–(6) were mixed and ground to obtain a powder portion. A liquid portion of (7)–(11) were mixed and dissolved. The powder portion was added to the liquid portion, whereby the powder portion was dispersed therein. Thereafter, the resultant foundation was separately filled in containers.

Example I-5

Premake up

| | |
|---|---|
| (1) Torayfil E-506C | 2.0 wt % |
| (2) Spherical nylon powder | 5.0 |
| (3) Finely divided titanium dioxide | 4.0 |
| (4) Octamethyl cyclotetrasiloxane | 10.0 |
| (5) Dimethyl polysiloxane (6 cs) | 8.0 |
| (6) Polyether modified silicone*[1] | 40.0 |
| (7) Sorbitan sesquiisostearate | 2.0 |
| (8) 1,3-Butyleneglycol | 5.0 |
| (9) Glycerol | 3.0 |
| (10) Solid paraffin | 5.0 |
| (11) Octylmethoxy cinnamate | 2.8 |
| (12) Methyl parabene | 0.2 |
| (13) Purified water | Balance |
| | 100.0 |

*see Table I-1

Method of Preparation

The ingredients (1)–(3) were mixed and ground to form a power portion (4)–(7) and (11) were mixed with heating to obtain an oil phase portion. The ingredients (8), (9) and (12) were dissolved in (13) to form an aqueous phase portion. The powder portion was dispersed in the heated oil phase portion at 70° C., followed by adding the heated aqueous phase portion at 70° C. to thereby be emulsified. Thereafter, the ingredient (10) previously melted at 80° C. or more, followed by subjecting to an emulsification treatment again. After deaeration, the product was filled in a container, followed by cooling.

Example I-6

Creamy Gelatinous Foundation

| | |
|---|---|
| (1) Stearyl alcohol | 1.2 wt % |
| (2) Behenyl alcohol | 1.2 |
| (3) Batyl alcohol | 1.0 |
| (4) Torayfil E-506C | 2.0 |
| (5) Decamethyl cyclopentasiloxane | 9.0 |
| (6) Polyether modified silicone*[1] | 4.0 |
| (7) Dimethyl polysiloxane | 3.0 |
| (8) Methylphenyl polysiloxane | 2.0 |
| (9) Squalane | 3.0 |
| (10) 2-Ethyl hexanoic acid triglyceride | 3.0 |
| (11) Glyceryl monostearate | 1.8 |
| (12) Stearic acid | 2.0 |
| (13) POE (60) hydrogenated castor oil | 0.5 |
| (14) Triethanolamine | 1.6 |
| (15) Ethylparaben | 0.2 |
| (16) Talc | 3.0 |

-continued

| | |
|---|---|
| (17) Sericite | 4.0 |
| (18) Mica | 3.0 |
| (19) Titanium dioxide | 1.0 |
| (20) Colored pigment | 3.0 |
| (21) Purified water | Balance |
| | 100.0 |

Method of Preparation

The ingredients (1)–(3), (5)–(13) and (15) were dissolved with heating to prepare the oil phase portion. To a heated aqueous phase portion at 70° C. obtained by dissolving (14) in (21), the heated oil phase portion at 70° C. was added and emulsified. Thereafter, the powder portion was dispersed therein. After deaerating, the product was cooled with stirring and filled in a container.

The make-up cosmetic compositions of Examples 2–6 all exhibited excellent cosmetic persistency effect.

As explained above, according to the present invention, the cosmetic persistency effects of the make-up cosmetics can be remarkably improved.

Examples II-1 to II-4 and Comparative Examples II-1 to II-4

External skin treatment compositions were prepared by the formulations described in Table II-1 and Table II-2 by the following methods. Their properties and, in the case of gels, their useabilities were evaluated.

TABLE II-1

| | Examples | | | |
|---|---|---|---|---|
| | II-1 | II-2 | II-3 | II-4 |
| (1) Torayfil E-506C (made by Toray Dow Corning) | 1.0 | 10.0 | 20.0 | 1.0 |
| (2) Spherical polyethylene powder | — | — | — | — |
| (3) Decamethyl cyclopentasiloxane | 30.0 | 45.0 | 50.0 | — |
| (4) Dimethyl polysiloxane (6 cs) | — | 15.0 | 26.0 | 30.0 |
| (5) Polyether modified silicone*[1] | 60.0 | 15.0 | 2.0 | 60.0 |
| (6) Microcrystalline wax | — | — | — | — |
| (7) Purified water | 6.0 | 8.0 | 1.0 | 6.0 |
| (8) Ethyl alcohol | 3.0 | 7.0 | 1.0 | 3.0 |
| Property | Gel | Gel | Gel | Gel |
| Useability | Good | Good | Good | Good |

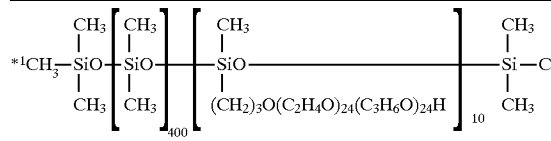

as a 50% decamethyl cyclopentasiloxane solution

TABLE II-2

| | Comparative examples | | | |
|---|---|---|---|---|
| | II-1 | II-2 | II-3 | II-4 |
| (1) Torayfil E-506C (made by Toray Dow Corning) | — | 10.0 | 0.5 | 20.0 |
| (2) Spherical polyethylene powder | 20.0 | — | — | — |
| (3) Decamethyl cyclopentasiloxane | 50.0 | 45.0 | 40.0 | 52.0 |
| (4) Dimethyl polysiloxane (6 cs) | 26.0 | 15.0 | 45.0 | 26.0 |
| (5) Polyether modified silicone*[1] | 2.0 | — | 0.5 | 2.0 |
| (6) Microcrystalline wax | — | — | 8.0 | — |
| (7) Purified water | 1.0 | 10.0 | 1.0 | — |
| (8) Ethyl alcohol | 1.0 | 20.0 | 5.0 | — |
| Property | Gel | Two layers separate (liquid) | Gel. | Gel |
| Useability | — | — | Sticky | Heavy spread-ability |

*[1]See in Table II-1

Method of Preparation

The ingredients (3) and (4) were mixed with stirring. When formulating (6), the mixture was heated to dissolve, then the powder (1) or (2) was dispersed and (5) added to make an oil phase part. (7) and (8) were mixed with stirring to make the aqueous phase which was then added to the oil phase with stirring. The mixture was stirred until it became homogeneous, then was deaerated. When not including (6), the process is performed under room temperature. When including (6), the process after the addition of (6) is performed at 70° C. After the entire process is completed, the mixture is cooled to room temperature.

As will be understood from Table II-1 and Table II-2, Examples II-1 to II-3 give gelatinous external skin treatment compositions having a superior useability.

Comparative Example II-1 used the spherical resin powder (2) instead of (1) compared with Example II-3, but it does not become gelatinous.

Comparative Example II-2 omits (5) compared with Example II-2, so will no gel. The two layers therefore separate.

Comparative Example II-3 has less of an amount of (5) and includes a wax component, so while a gel, has a heavy “spreadability”, is sticky, and is unsatisfactory in terms of useability.

Example II-5

Gelatinous Foundation

| | |
|---|---|
| (1) Silicone treated talc | 5.0 wt % |
| (2) Silicone treated sericite | 3.0 |
| (3) Silicone treated mica | 3.0 |
| (4) Silicone treated titaniumn oxide | 6.0 |
| (5) Silicone treated coloring pigment | 3.0 |
| (6) Torayfil E-506C | 8.0 |
| (7) Decamethyl cyclopentasiloxane | 50.0 |
| (8) Polyether modified silicone*[2] | 12.0 |
| (9) Diglycerine diisostearate | 1.0 |
| (10) Ethyl alcohol | 6.0 |
| (11) Purified water | 3.0 |

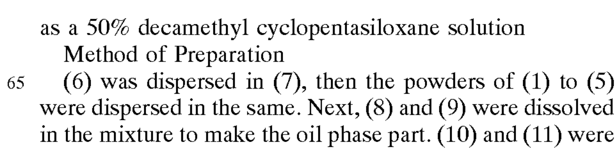

as a 50% decamethyl cyclopentasiloxane solution

Method of Preparation (6) was dispersed in (7), then the powders of (1) to (5) were dispersed in the same. Next, (8) and (9) were dissolved in the mixture to make the oil phase part. (10) and (11) were mixed to form the aqueous phase part which was then added into the oil phase part with stirring. The mixture was deaerated, then filled into a container to make a gelatinous foundation.

Example II-6

Premake up Gel

| | | |
|---|---|---|
| (1) | Torayfil E-506C | 8.0 wt % |
| (2) | Spherical nylon powder | 5.0 |
| (3) | Particulate titanium oxide | 3.0 |
| (4) | Octamethyl cyclotetrasiloxane | 22.0 |
| (5) | Decamethyl cyclopentasiloxane | 25.0 |
| (6) | Dimethyl polysiloxane (6 cs) | 11.0 |
| (7) | Polyether modified silicone*[1] | 13.0 |
| (8) | 1,3-butylene glycol | 2.0 |
| (9) | Sorbitan sesquistearate | 1.0 |
| (10) | Purified water | 9.8 |
| (11) | Methylparaben | 0.2 |

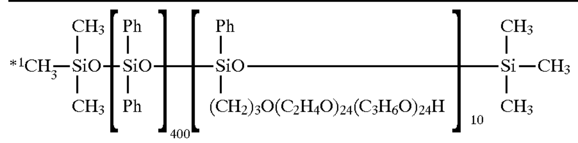

as a 50% decamethyl cyclopentasiloxane solution, where Ph indicates a phenyl group Method of Preparation The ingredients (4), (5), (6), and (9) were mixed with stirring, then the powders of (1), (2), and (3) were dispersed in it. Next, (7) was dissolved in this to make an oil phase part. (11) was dissolved in (10) to make an aqueous phase part which was then added into the oil phase part with stirring. The mixture was deaerated, then filled into a container to make a premake gel.

Example II-7

Sun Screen Gel

| | | |
|---|---|---|
| (1) | Dimethyl polysiloxane (6 cs) | 19.8 wt % |
| (2) | Octamethyl cyclotetrasiloxane | 30.0 |
| (3) | Torayfil E-506C | 12.0 |
| (4) | Polyether modified silicone*[1] | 20.0 |
| (5) | Octyl methoxycinnamate | 8.0 |
| (6) | Purified water | 8.0 |
| (7) | Methyl alcohoi | 2.0 |
| (8) | Methylparaben | 0.2 |

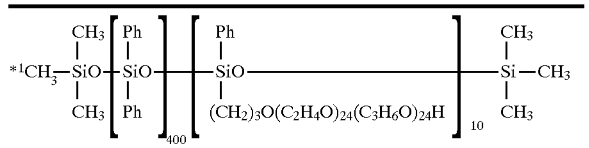

as a 50% decamethyl cyclopentasiloxane solution where Ph indicates a phenyl group Method of Preparation The ingredients (1), (2), (4), and (5) were mixed with stirring, then the powder of (3) was dispersed in it. Next, (7) and (8) were dissolved in (6) to make an aqueous phase part which was then added into the oil phase part with stirring. The mixture was deaerated, then filled into a container to make a sun screen gel.

The gelatinous external skin treatment compositions of Examples II-5 to II-7 are all superior in useability.

As explained above, the gelatinous external skin treatment compositions of the present invention have a good "spreadability", are free from stickiness, and the useability is remarkably improved.

Example II-8

Gelatinous Foundation

| | | |
|---|---|---|
| (1) | Silicone treated talc | 5.0 wt % |
| (2) | Silicone treated sericite | 3.0 |
| (3) | Silicone treated mica | 3.0 |
| (4) | Silicone treated titanium oxide | 6.0 |
| (5) | Silicone treated coloring pigment | 3.0 |
| (6) | Torayfil E-506C | 3.0 |
| (7) | Decamethyl cyclopentasiloxane | 51.0 |
| (8) | Polyether modified silicone*[1] | 16.0 |
| (9) | Diglycerine diisostearate | 1.0 |
| (10) | Ethyl alcohol | 6.0 |
| (11) | Purified water | 3.0 |

*[1]See in Table II-1

Method of Preparation (6) was dispersed in (7), then the powders of (1) to (5) were dispersed in the same. Next, (8) and (9) were dissolved in the mixture to make the oil phase part. (10) and (11) were mixed to form the aqueous phase part which was then added into the oil phase part with stirring. The mixture was deaerated, then filled into a container to make a gelatinous foundation.

I claim:

1. A gelatinous external skin treatment composition comprising:

(1) 1.0 to 20.0% by weight of spherical powder of organopolysiloxane elastomer having an average particle size of 1.0 to 15.0 μm;

(2) 5.0 to 75.0% by weight of silicone oil;

(3) 1.0 to 20.0% by weight of polyether modified silicone having the formula (I):

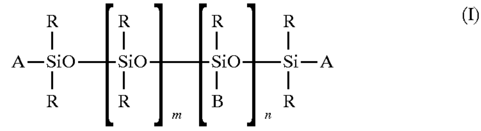

wherein A represents a methyl group, phenyl group, B is a polyoxyalkylene group having the formula:

$$-C_3H_6O(C_2H_4O)_a(C_3H_6O)_bR'$$

wherein R' is a group selected from the group consisting of a hydrogen atom, acyl group, and $C_1$ to $C_4$ alkyl groups, a is an integer of 5 to 50, and b is an integer of 5 to 50, R is a methyl group or phenyl group, m is an integer of 50 to 1000, and n is an integer of 0 to 40, provided that at least one polyoxyalkylene group is present in the molecule; and (4) 1.0 to 15.0% by weight of a component selected from the group consisting of lower alcohols having 3 carbon atoms or less and water.

2. A gelatinous external skin treatment composition as claimed in claim 1, wherein the silicone oil is dimethyl cyclopolysiloxane.

3. A gelatinous external skin treatment composition comprising:

(1) 1.0 to 20.0% by weight of spherical powder of organopolysiloxane elastomer having an average particle size of 1.0 to 15.0 μm;

(2) 25.0 to 85.0% by weight of silicone oil;

(3) 1.0 to 30.0% by weight of a polyether modified silicone having the general formula (I):

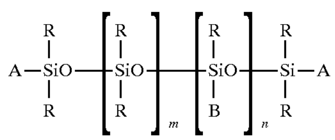

wherein A represents a methyl group, phenyl group, B is a polyoxyalkylene group having the formula:

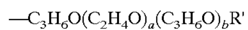

wherein R' is a group selected from the group consisting of a hydrogen atom, acyl group, and $C_1$ to $C_4$ alkyl groups, a is an integer of 5 to 50, and b is an integer of 5 to 50, R is a methyl group or phenyl group, m is an integer of 50 to 1000, and n is an integer of 0 to 40, provided that at least one polyoxyalkylene group is present in the molecule; and (4) 1.0 to 15.0% by weight of a component selected from the group consisting of lower alcohols having 3 carbon atoms or less and water.

4. A gelatinous external skin treatment composition as claimed in claim 3, wherein the amount of the component (1) is 5.0 to 20.0% by weight, the amount of the component (2) is 40.0 to 80.0% by weight, the amount of the component (3) is 2.0 to 20.0% by weight, and the amount of the component (4) is 5.0 to 12.0% by weight.

* * * * *